(12) United States Patent
Martens et al.

(10) Patent No.: US 9,388,107 B2
(45) Date of Patent: Jul. 12, 2016

(54) PROCESS FOR THE PRODUCTION OF A MIXTURE COMPRISING CYCLOHEXANONE AND CYCLOHEXANOL FROM PHENOL

(71) Applicant: CAP III B.V., Sittard (NL)

(72) Inventors: Wilhelmus Rudolf Maria Martens, Echt (NL); Robert Jan De Korte, Echt (NL); Iris Verschuren, Echt (NL); Corinne Daguenet, Echt (NL); Johan Thomas Tinge, Echt (NL); Roeland Wilhelmus Theodorus Maria Brands, Echt (NL)

(73) Assignee: CAP III B.V., Sittard (NL)

( * ) Notice: Subject to any disclaimer, the term of this patent is extended or adjusted under 35 U.S.C. 154(b) by 0 days.

(21) Appl. No.: 14/408,614

(22) PCT Filed: Jun. 27, 2013

(86) PCT No.: PCT/EP2013/063529
§ 371 (c)(1),
(2) Date: Dec. 17, 2014

(87) PCT Pub. No.: WO2014/001461
PCT Pub. Date: Jan. 3, 2014

(65) Prior Publication Data
US 2015/0158802 A1 Jun. 11, 2015

(30) Foreign Application Priority Data
Jun. 28, 2012 (EP) .................................. 12174157

(51) Int. Cl.
| | |
|---|---|
| *C07C 45/00* | (2006.01) |
| *C07C 29/00* | (2006.01) |
| *C07C 51/00* | (2006.01) |
| *C07C 29/20* | (2006.01) |
| *C07C 35/08* | (2006.01) |
| *C07C 49/603* | (2006.01) |
| *C07D 223/10* | (2006.01) |

(52) U.S. Cl.
CPC .............. *C07C 45/006* (2013.01); *C07C 29/20* (2013.01); *C07C 35/08* (2013.01); *C07C 49/603* (2013.01); *C07C 51/00* (2013.01); *C07D 223/10* (2013.01); *C07C 2101/14* (2013.01)

(58) Field of Classification Search
CPC ..... C07C 45/006; C07C 29/132; C07C 51/09; C07C 51/313; C07C 201/02
USPC ........... 568/362, 835, 876; 562/590; 540/534; 422/129
See application file for complete search history.

(56) References Cited

U.S. PATENT DOCUMENTS 2,829,166 A * 4/1958 Joris et al. ..................... 568/362

OTHER PUBLICATIONS

International Search Report for PCT/EP2013/063529 mailed Sep. 6, 2013.
A. Dimian et al., "Phenol Hydrogenation to Cyclohexanone", Chemical Process Design: Computer-Aided Case Studies, Mar. 3, 2008, pp. 129-172.

* cited by examiner

*Primary Examiner* — Sikarl Witherspoon
(74) *Attorney, Agent, or Firm* — Nixon & Vanderhye P.C.

(57) ABSTRACT

The present invention provides a process for continuously preparing a mixture of cyclohexanone and cyclohexanol comprising, a) hydrogenating phenol with gaseous hydrogen, in the presence of platinum or palladium, in a hydrogenation reactor, to produce a hydrogenation product stream comprising cyclohexanone, cyclohexanol, phenol and hydrogen; b) cooling the hydrogenation product stream to a temperature such that the fraction of phenol by mass in a first gas phase is lower than the fraction of phenol by mass in a first liquid phase; c) separating the first gas phase from the first liquid phase; d) returning at least part of the first gas phase to the hydrogenation reactor; e) heating the first liquid phase; f) purifying the first liquid phase by distillation; characterized in that heat is transferred from the hydrogenation product stream in step b) to another part of the process by means of in-process heat exchange; a mixture of cyclohexanone and cyclohexanol obtained by the process; and a chemical plant suitable for continuously preparing mixture of cyclohexanone and cyclohexanol according to the process.

11 Claims, 6 Drawing Sheets

PROCESS FOR THE PRODUCTION OF A MIXTURE COMPRISING CYCLOHEXANONE AND CYCLOHEXANOL FROM PHENOL

This application is the U.S. national phase of International Application No. PCT/EP2013/063529 filed 27 Jun. 2013 which designated the U.S. and claims priority to EP 12174157.3 filed 28 Jun. 2012, the entire contents of each of which are hereby incorporated by reference.

FIELD

The invention relates to a process for the preparation of a mixture comprising cyclohexanone and cyclohexanol from phenol; to a mixture produced by said process and to a plant for preparing said mixture.

BACKGROUND AND SUMMARY

A mixture of cyclohexanone and cyclohexanol can be employed as an industrial solvent or as an activator in oxidation reactions. It can also be used as an intermediate, for example in the production of adipic acid or nylon 6,6. Where the mixture is mostly or almost entirely cyclohexanone, this can be used in the production of cyclohexanone resins, caprolactam or nylon 6.

Mixtures of cyclohexanone and cyclohexanol are conventionally prepared from phenol by catalytic hydrogenation in a phenol hydrogenation reactor, e.g. using a platinum or a palladium catalyst. The reaction can be carried out in the liquid phase or the vapour phase. [Kirk-Othmer Encyclopedia of Chemical Technology, e.g. $3^{rd}$ Edition, Vol 7 (1979) p. 410-416; I. Dodgson et al. "A low Cost Phenol to Cyclohexanone Process", Chemistry & Industry, 18, December 1989, p 830-833; or M. T. Musser "Cyclohexanol and Cyclohexanone", Ullmann's Encyclopedia of Industrial Chemistry 7th Edition, 2007), (hereafter "Musser")].

In the preparation of cyclohexanone from phenol, typically cyclohexanol (which can be considered an intermediate product useful for further conversion to cyclohexanone) and various undesirable by-products are formed.

The cyclohexanone is typically recovered by a distillation process as a mixture of cyclohexanone and cyclohexanol (usually ≥90 wt. % cyclohexanone) or as an essentially pure product (≥99 wt. %).

A conventional process for the preparation of a mixture of cyclohexanone and cyclohexanol from phenol feedstock involves hydrogenation of phenol with gaseous hydrogen in the presence of platinum or palladium in a hydrogenation reactor, to produce a hydrogenation product stream comprising cyclohexanone, cyclohexanol, phenol and hydrogen; cooling the hydrogenation product stream to a temperature, such that the fraction of phenol by mass in a first gas phase is lower than the fraction of phenol by mass in a first liquid phase; separating the first gas phase from the first liquid phase; returning at least part of the first gas phase to the hydrogenation reactor; heating the first liquid phase; and purification of the first liquid phase by distillation. Such a process is described schematically in FIG. 1. In such a process, cooling is necessary to aid separation of hydrogen from the hydrogenation product stream. Heating of the first liquid phase is needed to prepare it for distillation. Typically the separated first gas phase which contains hydrogen is heated before returning it to the hydrogenation reactor.

A problem in the above described processes is that consumption of steam for heating is high. In particular a large amount of energy is used for heating both the first liquid phase, and the first gas phase. At the same time, cooling is applied, meaning that cooling water is required to transfer heat from the process stream. Both heating and cooling accordingly increase cost and carbon foot print of the process as a whole.

It is therefore an object of the present invention to provide a method for preparing a mixture of cyclohexanone and cyclohexanol, wherein the above drawbacks are overcome or at least alleviated.

The present inventors have found that it is possible to reduce energy consumption and reduce the consumption of cooling water and improve the carbon foot print in a process for converting phenol to a mixture of cyclohexanone and cyclohexanol by hydrogenation by introducing one or more additional in-process heat exchange steps. Specifically, heat transferred from the hydrogenation product stream as it is cooled is transferred to another part of the process stream which requires heating.

Accordingly, the present invention provides a process for continuously preparing a mixture of cyclohexanone and cyclohexanol comprising, a) hydrogenating phenol with gaseous hydrogen, in the presence of platinum or palladium, in a hydrogenation reactor, to produce a hydrogenation product stream comprising cyclohexanone, cyclohexanol, phenol and hydrogen;
b) cooling the hydrogenation product stream to a temperature such that the fraction of phenol by mass in a first gas phase is lower than the fraction of phenol by mass in a first liquid phase;
c) separating the first gas phase from the first liquid phase;
d) returning at least part of the first gas phase to the hydrogenation reactor;
e) heating the first liquid phase;
f) purifying the first liquid phase by distillation;
characterized in that heat is transferred from the hydrogenation product stream in step b) to another part of the process by means of in-process heat exchange.

DETAILED DESCRIPTION

Figure 1:
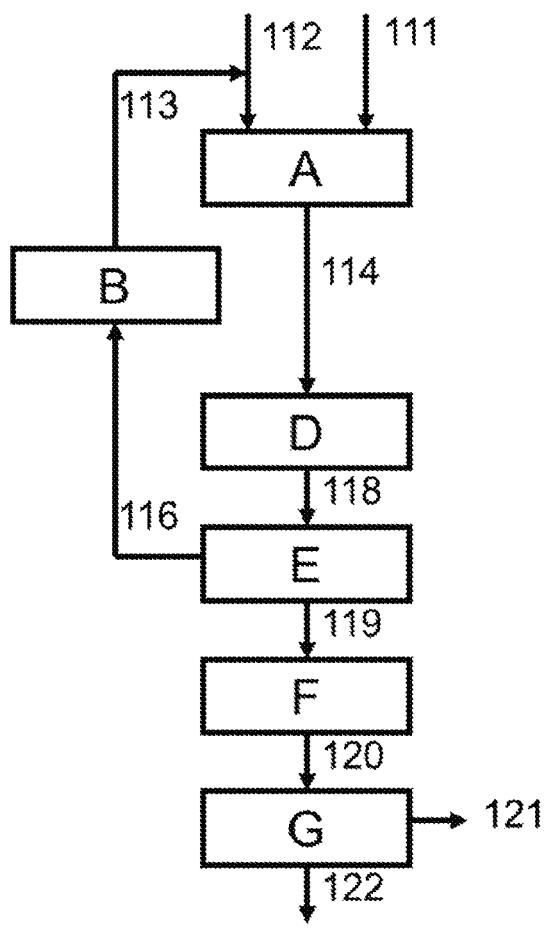
FIG. 1 is a schematic diagram of a conventional process for the preparation of a mixture of cyclohexanone and cyclohexanol from phenol feedstock involves hydrogenation of phenol with gaseous hydrogen in the presence of platinum or palladium in a hydrogenation reactor.

The present invention further provides a mixture of cyclohexanone and cyclohexanol obtained by said process. Further, the present invention provides a chemical plant suitable for continuously preparing a mixture of cyclohexanone and cyclohexanol, as described above.

As indicated above, the process of the invention comprises the synthesis of a mixture of cyclohexanone and cyclohexanol and a number of distillation steps to recover a mixture of cyclohexanone and cyclohexanol.

As used herein a mixture of cyclohexanone and cyclohexanol means a mixture of these two compounds in any proportion. It may also include impurities, for example by-products of the hydrogenation reaction, in an amount of up to 2 wt %, preferably up to 0.5 wt %. Typically, cyclohexanone is the major component of the mixture. Cyclohexanol may be considered an intermediate in the production of cyclohexanone. For some applications, e.g. manufacture of caprolactam, it is cyclohexanone that is preferred. Cyclohexanone may therefore be the vast majority of the mixture. Accordingly, in one embodiment typically the mixture of cyclohexanol and cyclohexanone comprises at least 90 wt % cyclohexanone. Preferably it comprises 95 wt %; more preferably 99 wt %; yet more preferably at least 99.5 wt % cyclohexanone. Most preferably, the mixture of cyclohexanol and cyclohexanone comprises at least 99.85 wt % cyclohexanone.

The hydrogenation of phenol can in principle be carried out in any way, in a vapour phase or in a liquid phase, e.g. based on any technology described in or referred to in Kirk-Othmer Encyclopedia of Chemical Technology $3^{rd}$ Edition, Vol 7, 1979 p. 410-416; I. Dodgson et al. "A low Cost Phenol to Cyclohexanone Process", Chemistry & Industry, 18, December 1989, p 830-833; GB 890,095; Hancil and Beranek Chem. Eng. Sci., 25, 1970, p. 1121-1126; or Sakai et al. Nippon Kagaku Kaishi, 5, 1972, 821-829; Musser (in Ullmans's, see above); U.S. Pat. No. 2,829,166 or U.S. Pat. No. 3,076,810. The hydrogenation reaction section may comprise an internal recycling stream for recycling part of the stream leaving a reactor wherein the hydrogenation takes place. The hydrogenation product stream leaving the hydrogenation reaction section generally comprises cyclohexanone, cyclohexanol, phenol, by-products and inerts.

The hydrogenation may be carried out in the gas phase, the liquid phase or a gas-liquid mixture. Typically the hydrogenation is carried out in the gas phase.

The hydrogenation product stream is cooled in order to at least partially condense it. Hydrogen is the last component to condense, so cooling increases the fraction of hydrogen in the gas phase. It is desired to separate hydrogen for recycle to the hydrogenation reactor. The hydrogen content in the gas phase and liquid phase can be calculated from measurement by standard techniques known in the art, for example by gas-liquid chromatography of a sample.

Separation is carried out by standard techniques using a commercially available gas-liquid separator. At least part of the first gas phase is returned to the hydrogenation reactor. This may be directly to the reactor, or it may be first combined with the feed of hydrogen gas. Typically the remaining part of the first gas phase is purged from the system.

The first liquid phase is heated in order to prepare it for distillation. This is commonly known as preheating.

Distillation can be accomplished in a manner known in the art. Suitable distillation conditions can routinely be determined by the skilled person, based on common general knowledge and routine experimentation. In particular the skilled person may consult the prior art cited herein.

In distillation, a fluid is separated into at least two fractions. When comparing two fractions, one may be called a light fraction, the other a heavy fraction. In particular when reference is made herein to a light fraction or a heavy fraction in relation to a separation by distillation, these terms are used herein relative to each other in a specific distillation step, to distinguish the fraction with the lower boiling point (the light fraction) from the fraction with the higher boiling point (the heavy fraction). As generally known, separation of a mixture into a heavy fraction and a light fraction is never absolute.

A distillation section, as used herein, is an installation comprising one distillation column or a plurality of distillation columns in parallel, which may have the same or different functionality; or a plurality of columns in series, which may have the same or different functionality. Further this section may comprise other typical parts of distillation units. Suitable distillation conditions are known in the art, see, for example, U.S. Pat. No. 2,829,166 or U.S. Pat. No. 3,076,810.

In-process heat exchange is typically done through a conventional in-process heat exchanger. An in-process heat exchanger is an indirect heat exchanger (wherein the fluid streams remain separated by a dividing wall) wherein a process fluid from one part of the process transfers heat to a process fluid in another part of the process without direct contact of the fluids. It might be that during the process of heat transfer one or more components are partially or (almost) completely condensated or evaporated.

Indirect heat exchangers are well-known to the person of skill in the art. Examples of indirect heat exchangers suitable for the present invention are shell & tube, plate, and tubular. Typically the indirect heat exchanger comprises a shell & tube indirect heat exchanger. A shell & tube indirect heat exchanger is preferred, because it is capable of handling a large flow.

In one embodiment of the present invention a process is provided wherein heat is transferred from the hydrogenation product stream in step b) to the at least part of the first gas phase in step d) by means of in-process heat exchange. Before the hydrogenation product stream and the first gas phase each enter the in-process heat exchanger, the temperature of the hydrogenation product stream is higher than that of the first gas phase. The hydrogenation product stream is therefore used to heat the first gas phase. In other words, the in-process heat exchanger is configured such that the hydrogenation product stream heats the first gas phase and that the hydrogen containing first gas phase cools the hydrogenation product stream. Typically, the at least part of the first gas phase is heated to a temperature of from 50 to 200° C.

In another embodiment of the present invention a process is provided wherein heat is transferred from the hydrogenation product stream in step b) to the first liquid phase in step e) by means of in-process heat exchange. Before the hydrogenation product stream and the first liquid phase each enter the in-process heat exchanger, the temperature of the hydrogenation product stream is higher than that of the first liquid phase. In the present invention, therefore, the hydrogenation product stream is used to heat the first liquid phase. In other words, the in-process heat exchanger is configured such that the hydrogenation product stream heats the first liquid phase and that the first liquid phase cools the hydrogenation product stream. Typically, the hydrogenation product stream is cooled in step b) to a temperature of from 5 to 80° C. Typically, the first liquid phase is heated in step e) to a temperature of from 50 to 200° C.

In one embodiment heat is transferred from the hydrogenation product stream in step b) to both the first liquid phase in step e) and to the at least part of the first gas phase in step d).

In one embodiment, the invention further provides a process wherein step f) comprises f1) removing a light fraction by distillation; f2) recovering as overhead product a mixture of cyclohexanone and cyclohexanol; f3) recovering as overhead product a fraction comprising at least 50 wt % cyclohexanol; f4) recovering as overhead product a phenol-containing fraction; f5) returning at least a part of the phenol-containing fraction to the hydrogenation reactor; and f6) removing as bottom product a heavy fraction. Preferably, the overhead fraction recovered in step f3) comprises at least 70 wt %, more preferably at least 80 wt %, yet more preferably at least 90 wt % cyclohexanol.

Typically, this embodiment further comprises partially converting to cyclohexanone the cyclohexanol in the fraction comprising at least 50 wt % cyclohexanol. Said conversion is typically cyclohexanol dehydrogenation. Cyclohexanol dehydrogenation is described in, for example, Musser, at paragraph 3.5.

Preferably, the process further comprises i) cooling the partially converted fraction comprising at least 50 wt % cyclohexanol to form a second liquid phase and a second gas phase; ii) separating the second gas phase; iii) heating the second liquid phase; and iv) purifying the second liquid phase by distillation. Preferably said distillation is in the same apparatus as distillation of the first liquid phase. Accordingly, the second liquid phase is combined with the first liquid phase, to form a combined liquid phase. This may be done at any suitable point in the distillation process. Preferably, the second liquid phase is combined with the first liquid phase to form a combined liquid phase; and heat is transferred from the hydrogenation product stream in step b) to the combined liquid phase in step e) by means of in-process heat exchange. Accordingly, a further heat integration is achieved. The hydrogenation product stream heats both the first liquid phase and the second liquid phase. Therefore heating of these phases by steam is either reduced or eliminated, by use of in-process heat exchange.

The present invention further comprises converting the mixture of cyclohexanone and cyclohexanol into caprolactam or adipic acid. These end-products can be obtained by processes known in the art. When the desired product is caprolactam, a mixture of cyclohexanone and cyclohexanol with a proportion of cyclohexanone as high as possible is preferred. Most preferably there is substantially no cyclohexanol in the mixture of cyclohexanone and cyclohexanol. When the desired product is adipic acid, then any mixture of cyclohexanone and cyclohexanol may be used.

As will be understood by the skilled person, the embodiments illustrated as examples in FIGS. 2, 3, 4, 5 and 6, discussed herein below in more detail, or parts thereof may be combined to provide alternative embodiments of the invention. It is to be noted that the feed streams to numbered sections are represented as separate streams, but it will be evident to the skilled person that streams fed into a section may be combined before entering the section, or may enter the section separately. For example, streams fed into a section may be introduced into a distillation column of the section at different levels of the column.

FIG. 1 represents an embodiment of a prior art process, in which the present invention has not been implemented. Fresh phenol is provided through feed [111] and hydrogen gas is provided through line [112]. These are reacted in hydrogenation section [A], which comprises at least one hydrogenation reactor, in the presence of platinum or palladium. The resulting hydrogenation product stream comprising cyclohexanone, cyclohexanol, by-products, unreacted phenol, hydrogen and inert compounds, passes through line [114] into cooling unit [D] which comprises one or more indirect heat exchangers. Cooling water is used as coolant. The cooled hydrogenation reaction mixture leaving cooling unit [D] consists of a first liquid phase, comprising mainly cyclohexanol, cyclohexanone, phenol and by-products, and a hydrogen containing first gas phase The cooled hydrogenation product stream is then passed via line [118] into gas-liquid separation section [E] which comprises one or more gas-liquid separators. The first gas phase is discharged via line [116] to heating unit [B] which comprises one or more indirect heat exchangers and uses steam as heat source. The heated first gas phase is then passed via line [113] to line [112], where it is mixed with hydrogen gas. The first liquid phase, comprising mainly cyclohexanone, cyclohexanol, phenol and by-products, is passed via line [119] into heat transfer unit [F], which comprises one or more indirect heat exchangers, where it is heated. The heated flow is discharged via line [120] to purification section [G]. Here, a mixture of cyclohexanone and cyclohexanol is recovered via line [121]. By-products are removed from the purification section [G] via line [122].

The by-products from the purification section [G] are typically incinerated or used for steam generation in a boiler house. Alternatively, the bottom fraction may be used as a low-cost material for a residual product, e.g. tar, asphalt, shoe polish or the like.

Figure 2:
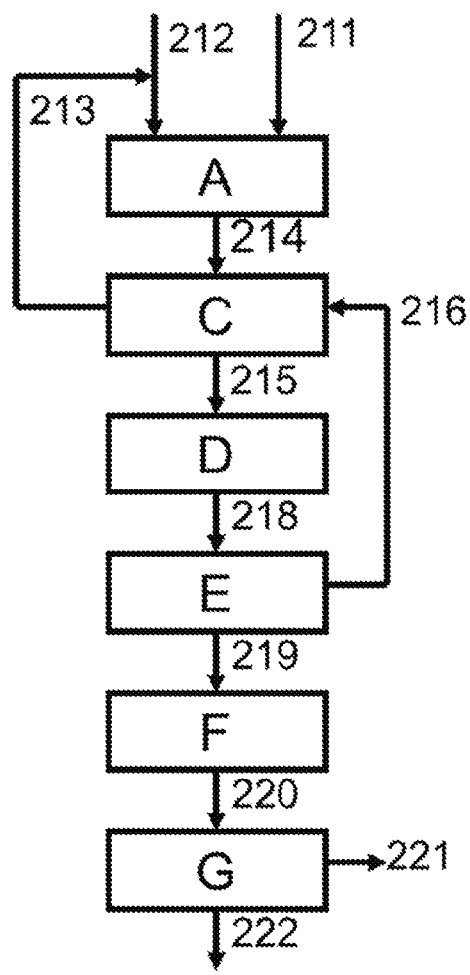
FIG. 2 is a schematic diagram of a first embodiment of the present invention.

FIG. 2 represents a first embodiment of the present invention. Fresh phenol is provided through feed [211] and hydrogen gas is provided through line [212]. These are reacted in hydrogenation section [A], which comprises at least one hydrogenation reactor, in the presence of platinum or palladium. The resulting hydrogenation product stream, comprising cyclohexanone, cyclohexanol, by-products, unreacted phenol, hydrogen and inert compounds, passes through line [214] into heat transfer unit [C] which comprises one or more indirect heat exchangers, where it is cooled. The cooled hydrogenation product stream leaves heat transfer unit [C] via line [215] and passes into cooling unit [D] which comprises one or more indirect heat exchangers, where it is further cooled. Cooling water is used as coolant. The cooled hydrogenation product stream leaving cooling unit [D] consists of a first liquid phase, comprising mainly cyclohexanol, cyclohexanone, phenol and by-products, and a hydrogen containing first gas phase. The cooled hydrogenation product stream is then passed via line [218] into gas-liquid separation section [E] which comprises one or more gas-liquid separators. The first gas phase is discharged via line [216] to heat transfer unit [C]. Here, the first gas phase is indirectly heated by the hydrogenation product stream. The heated first gas phase is then passed via line [213] to line [212], where it is mixed with hydrogen gas. The first liquid phase, comprising mainly cyclohexanone, cyclohexanol, phenol and by-products, is passed from gas-liquid separation section [E] via line [219] into heat transfer unit [F], which comprises one or more indirect heat exchangers, where it is heated. The heated flow is discharged via line [220] to purification section [G]. Here, a mixture of cyclohexanone and cyclohexanol is recovered via line [221]. By-products are removed from the purification section [G] via line [222].

Figure 3:
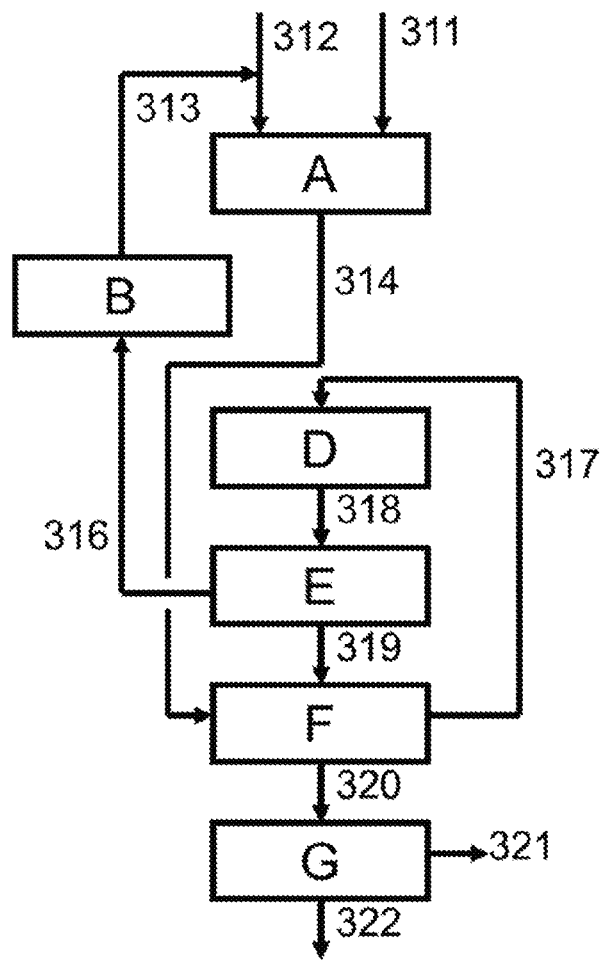
FIG. 3 is a schematic diagram of a second embodiment of the present invention.

FIG. 3 represents a second embodiment of the present invention. Fresh phenol is provided through feed [311] and hydrogen gas is provided through line [312]. These are reacted in hydrogenation section [A], which comprises at least one hydrogenation reactor, in the presence of platinum or palladium. The resulting hydrogenation product stream, comprising cyclohexanone, cyclohexanol, by-products, unreacted phenol, hydrogen and inert compounds passes through line [314] into heat transfer unit [F] which comprises one or more indirect heat exchangers. The cooled hydrogenation product stream leaves heat transfer unit [F] via line [317] and passes into cooling unit [D] which comprises one or more indirect heat exchangers, where it is further cooled. Cooling water is used as coolant. The cooled hydrogenation product stream leaving cooling unit [D] consists of a first liquid phase, comprising mainly cyclohexanol, cyclohexanone, phenol and by-products, and a hydrogen containing first gas phase. The cooled hydrogenation product stream is then passed via line [318] into gas-liquid separation section [E] which comprises one or more gas-liquid separators. The first gas phase is discharged via line [316] to heating unit [B] which comprises one or more indirect heat exchangers and uses steam as heat source. The heated first gas phase is then passed via line [313] to line [312], where it is mixed with hydrogen gas. The first liquid phase, comprising mainly cyclohexanone, cyclohexanol, phenol and by-products, is passed via line [319] into heat transfer unit [F], which comprises one or more indirect heat exchangers, where it is heated. The heated flow is discharged via line [320] to purification section [G]. Here, a mixture of cyclohexanone and cyclohexanol is recovered via line [321]. By-products are removed from the purification section [G] via line [322].

Figure 4:
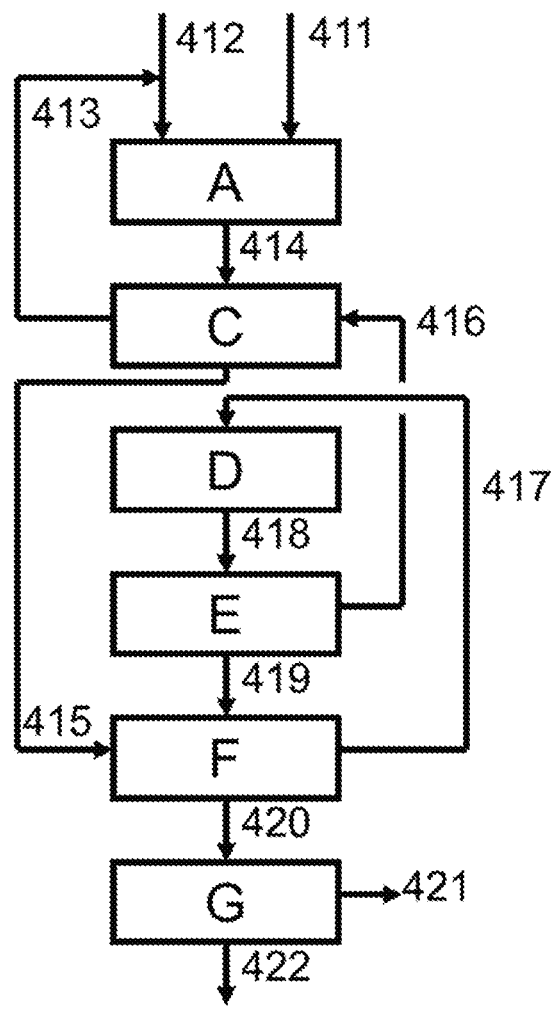
FIG. 4 is a schematic diagram of a third embodiment of the present invention.

FIG. 4 represents a third embodiment of the present invention. This embodiment is essentially a combination of the previous two embodiments. Fresh phenol is provided through feed [411] and hydrogen gas is provided through line [412]. These are reacted in hydrogenation section [A], which comprises at least one hydrogenation reactor, in the presence of platinum or palladium. The resulting hydrogenation product stream, comprising cyclohexanone, cyclohexanol, by-products, unreacted phenol hydrogen and inert compounds, passes through line [414] into heat transfer unit [C] which comprises one or more indirect heat exchangers, where it is cooled. The cooled hydrogenation product stream leaves heat transfer unit [C] via line [415] and passes into heat transfer unit [F] which comprises one or more indirect heat exchangers. The cooled hydrogenation product stream leaves heat transfer unit [F] via line [417] and passes into cooling unit [D] which comprises one or more indirect heat exchangers, where it is further cooled. Cooling water is used as coolant. The cooled hydrogenation product stream leaving cooling unit [D] consists of a first liquid phase, comprising mainly cyclohexanol, cyclohexanone, phenol and by-products, and a hydrogen containing first gas phase. The cooled hydrogenation product stream is then passed via line [418] into gas-liquid separation section [E] which comprises one or more gas-liquid separators. The first gas phase is discharged via line [416] to heat transfer unit [C]. Here, the first gas phase is indirectly heated by the hydrogenation product stream. The heated first gas phase is then passed via line [413] to line [412], where it is mixed with hydrogen gas. The first liquid phase, comprising mainly cyclohexanone, cyclohexanol, phenol and by-products, is passed from gas-liquid separation section [E] via line [419] into heat transfer unit [F], which comprises one or more indirect heat exchangers. The first liquid phase is indirectly heated by the hydrogenation product stream. The heated first liquid phase passes through line [420] to purification section [G]. Here, a mixture of cyclohexanone and cyclohexanol is recovered via line [421]. By-products are removed from the purification section [G] via line [222].

Figure 5:
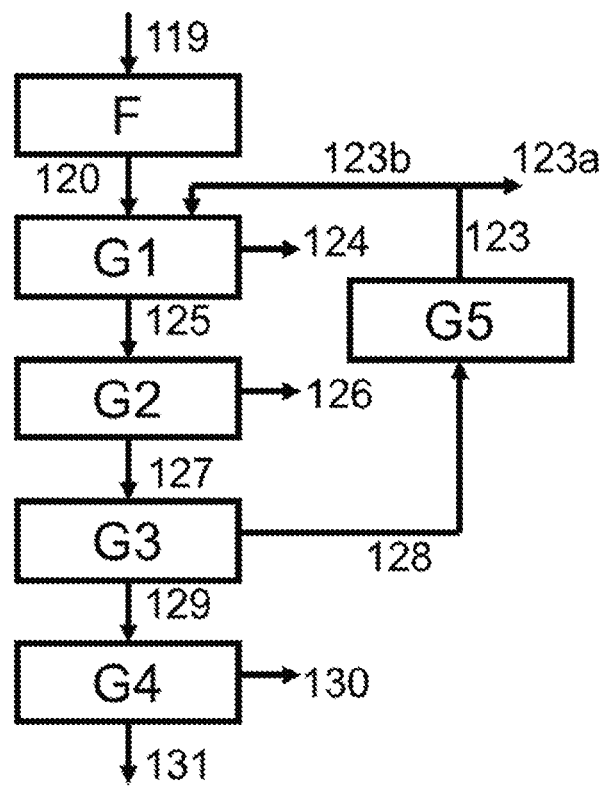
FIG. 5 is a schematic diagram of a purification section that may be employed in the processes embodying the present invention.

FIG. 5 represents an embodiment of the purification part of the process (purification section [G]). The first liquid phase (as described in FIG. 2, 3 or 4), from earlier in the process, passes via line [119] into heat transfer unit [F] where it is heated and passed via line [120] to first distillation section [G1]. Light components are removed as overhead product via line [124]. The bottom product of first distillation section [G1] is passed via line [125] to second distillation section [G2]. Cyclohexanone is removed as overhead product via line [126]. The bottom product comprises phenol, cyclohexanol, cyclohexanone and various by-products, and is passed via line [127] to distillation section [G3]. From distillation section [G3] the overhead product is a cyclohexanol-rich mixture of cyclohexanone and cyclohexanol, and traces of by-products. This is passed via line [128] to cyclohexanol dehydrogenation section [G5]. Typically, cyclohexanol dehydrogenation section [G5] comprises a dehydrogenation reactor, and usually further an evaporator for evaporating the feed upstream of the reactor, and a condenser for condensing the product stream leaving the reactor. In cyclohexanol dehydrogenation section [G5], a part of the cyclohexanol in the mixture is dehydrogenated to cyclohexanone. The obtained mixture is then removed via line [123]. Part of the mixture is removed from the system via line [123a], and part is recycled via line [123b] to distillation section [G1]. The bottom product from distillation section [G3] is predominantly phenol. It is passed to distillation section [G4], where phenol and some remaining amounts of cyclohexanone and cyclohexanol are removed as overhead product via line [130]. The bottom product of distillation section [G4] is removed via line [131] and is typically either incinerated or used for steam generation in a boiler house. Alternatively, the bottom fraction may be used as a low-cost material for a residual product, e.g. tar, asphalt, shoe polish or the like.

Figure 6:
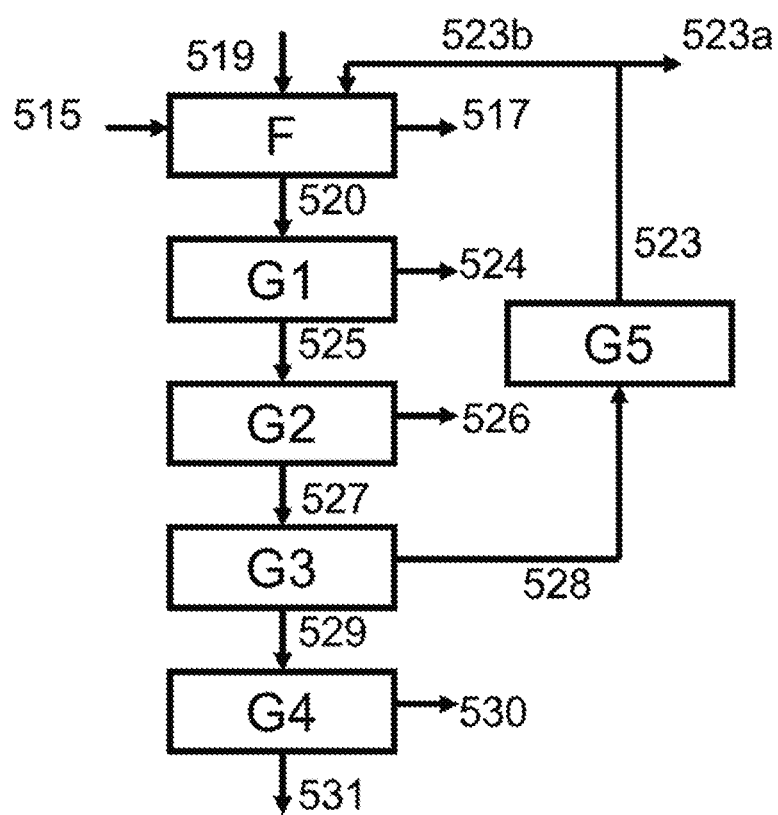
FIG. 6 is a schematic diagram of yet another embodiment of the present invention also showing the purification section thereof.

FIG. 6 represents a further embodiment of the present invention, again showing the purification part of the process (purification section [G]). The first liquid phase, from earlier in the process (as described in FIG. 2, 3 or 4), passes via line [519] into heat transfer unit [F] where it is heated. Heat is provided indirectly by the hydrogenation product stream, entering heat transfer unit [F] via line [515] and leaving, at lower temperature, via line [517]. The heated first liquid phase is passed via line [519] to first distillation section [G1]. Light components are removed as overhead product via line [524]. The bottom product of first distillation section [G1] is passed via line [525] to second distillation section [G2]. Cyclohexanone is removed as overhead product via line [526]. The bottom product comprises phenol, cyclohexanol, cyclohexanone and various by-products, and is passed via line [527] to distillation section [G3]. From distillation section [G3] the overhead product is a cyclohexanol-rich mixture of cyclohexanone and cyclohexanol. This is passed via line [528] to cyclohexanol dehydrogenation section [G5]. Typically, cyclohexanol dehydrogenation section [G5] comprises a dehydrogenation reactor, and usually further an evaporator for evaporating the feed upstream of the reactor, and a condenser for condensing the product stream leaving the reaction. In cyclohexanol dehydrogenation section [G5], a part of the cyclohexanol in the mixture is dehydrogenated to cyclohexanone. The mixture is then removed via line [523]. Part of the mixture is removed via line [523a] and part is recycled via line [523b] to heat transfer unit [F]. Here, it is mixed with first liquid phase and also heated indirectly by the hydrogenation product stream passing through heat transfer unit [F] via lines [515] and [517]. The bottom product from [G3] is predominantly phenol. It is passed to distillation section [G4], where phenol and some remaining amounts of cyclohexanone and cyclohexanol are removed as overhead product via line [530]. The bottom product of distillation section [G4] is removed via line [531] and is typically either incinerated or used for steam generation in a boiler house. Alternatively, the bottom fraction may be used as a low-cost material for a residual product, e.g. tar, asphalt, shoe polish or the like.

The present invention is illustrated by but not limited to the following examples.

EXAMPLES

Example 1 was carried out in an operating cyclohexanone plant, about 12 months after replacement of the hydrogenation catalyst in the phenol hydrogenation section [A]. For convenience of comparison with Example 1 according to the invention, the data for the Comparative Example and Examples 2 and 3 were calculated by modeling a cyclohexanone plant having the same capacity as the plant of Example 1 (in all cases at about 12 months after replacement of the hydrogenation catalyst in the phenol hydrogenation section [A]).

Comparative Example

A cyclohexanone plant consisting of a phenol hydrogenation reaction section [A]; a heating unit [B] consisting of shell-and-tube type indirect heat exchangers; a cooling unit [D] consisting of shell-and-tube type indirect heat exchangers; a gas-liquid separation section [E]; a heat transfer unit [F] consisting of shell-and-tube type indirect heat exchangers; a first distillation section [G1] for the removal of light components; a second distillation section [G2] wherein a product rich in cyclohexanone is recovered; a distillation section [G3] wherein a product rich in cyclohexanol is recovered; a distillation section [G4] wherein remaining valuable components, mainly phenol, are recovered; and a cyclohexanol dehydrogenation section [G5]; as described above with reference to FIGS. 1 and 5, is operated at an hourly mass flow of a mixture of cyclohexanone and cyclohexanol (comprising about 99.9 wt % cyclohexanone) leaving the second distillation section [G2], via line [126], of about 25 metric tons. From distillation section [G4] a bottom fraction is obtained which is used for steam generation in a boiler house.

The ratio of the sum of mole fractions of cyclohexanol and cyclohexanone in the vapor flow leaving the hydrogenation section [A] to the sum of mole fractions of cyclohexanol, cyclohexanone and phenol in the vapor flow leaving the hydrogenation section [A] is maintained at about 94 percent. The hydrogenation product stream leaving the hydrogenation section [A] has a temperature of about 180° C. and a pressure of about 0.2 MPa and flows through the inside of the tubes of the heat exchangers of cooling unit [D]. Cooling water is used as coolant and flows on the outside of the tubes of the heat exchangers of cooling unit [D]. The hydrogenation product stream leaving the cooling unit [D] is at a temperature of about 43° C. and is fed as a two-phase system to the gas-liquid separation section.

In the gas-liquid separation section [E] the gas phase and the liquid phase are separated in a gas-liquid separation vessel without additional reduction of pressure. The separated gas phase is re-used in the hydrogenation section [A]. Prior to re-use of this flow a fraction is purged in order to prevent the build-up of inert compounds, for example methane or nitrogen. The remaining gas flow is re-pressurized before being fed, via heating unit [B], where it is heated with steam to a temperature of about 165° C., to the hydrogenation section [A]. The liquid phase obtained in the gas-liquid separation vessel is heated with steam in heat transfer unit [F] to about 100° C. before being charged to first distillation section [G1].

The gaseous flow that is discharged from cyclohexanol dehydrogenation section [G5] via line [123] is cooled in a series of indirect heat exchangers (not shown in FIG. 5) to about 43° C. The resulting cooled flow consists of a liquid phase comprising mainly cyclohexanone, cyclohexanol, by-products and of a hydrogen containing gas phase. The cooled flow is then passed into a gas-liquid separation section (not shown in FIG. 5) in which it is split into a hydrogen-containing second gas phase and a second liquid phase comprising mainly cyclohexanone, cyclohexanol and by-products. The obtained second liquid phase is, after being heated to about 100° C. (not shown in FIG. 5), charged to a first distillation section [G1] via line [123b]. The hydrogen-containing second gas phase is discharged via line [123a].

Results are shown in Table 1.

Example 1

A cyclohexanone plant analogous to that of the Comparative Example was used, except that heating unit [B] was replaced by in-process heat transfer unit [C]. The set-up was therefore substantially as depicted in FIGS. 2 and 5. It is operated at an hourly mass flow of a mixture of cyclohexanone and cyclohexanol (comprising about 99.9 wt % cyclohexanone) leaving the second distillation section [G2], via line [126], of about 25 metric tons.

The ratio of the sum of mole fractions of cyclohexanol and cyclohexanone in the vapor flow leaving the hydrogenation section [A] to the sum of mole fractions of cyclohexanol, cyclohexanone and phenol in the vapor flow leaving the hydrogenation section [A] was similar to that in the Comparative Example. The heat transfer units [C] and [F] and cooling unit [D] each consisted of a series of shell-and-tube type indirect heat exchangers. The hydrogenation product stream leaving the hydrogenation section [A] had a temperature and a pressure that were almost equal to that in the Comparative Example. In cooling unit [D] cooling water was used as coolant and flowed on the outside of the tubes of the heat exchangers of the cooling unit [D]. The hydrogenation product stream leaving the cooling unit [D] was at a temperature of 43° C. and was fed as a two-phase system to the gas-liquid separation section [E].

In the gas-liquid separation section [E] the gas phase and the liquid phase were separated in a gas-liquid separation vessel without additional reduction of pressure. A major fraction of the gas phase was re-used in the hydrogenation section [A]. Prior to re-use of this flow a fraction was purged in order to prevent the build-up of inert compounds, for example methane or nitrogen. The remaining gas flow was re-pressurized before being fed, via heat transfer unit [C], where it was heated by the hydrogenation product stream leaving the hydrogenation section [A] to a temperature almost equal to that in the Comparative Example, to the hydrogenation section [A]. The liquid phase obtained in the gas-liquid separation vessel was heated with steam in heat transfer unit [F] to about the same temperature as that in the Comparative Example before being charged to first distillation section [G1].

The gaseous flow that is discharged from cyclohexanol dehydrogenation section [G5] via line [123] was cooled in a series of indirect heat exchangers (not shown in FIG. 5) to about 43° C. The resulting cooled flow consisted of a liquid phase comprising mainly cyclohexanone, cyclohexanol, by-products and of a hydrogen containing gas phase. The cooled flow was then passed into a gas-liquid separation section (not shown in FIG. 5) in which it is split into a hydrogen-containing second gas phase and a second liquid phase comprising mainly cyclohexanone, cyclohexanol and by-products. The obtained second liquid phase was, after being heated to about 100° C. (not shown in FIG. 5), charged to a first distillation section [G1] via line [123b]. The hydrogen-containing second gas phase was discharged via line [123a].

Results are shown in Table 1.

Example 2

A cyclohexanone plant analogous to that of the Example 1, except that heat transfer unit [F] is an in-process heat transfer unit is used. The set-up is therefore substantially as depicted in FIGS. 4 and 5. It is operated at an hourly mass flow of purified a mixture of cyclohexanone and cyclohexanol (comprising about 99.9 wt % cyclohexanone) leaving the second distillation section [G2], via line [126], of about 25 metric tons.

The ratio of the sum of mole fractions of cyclohexanol and cyclohexanone in the vapor flow leaving the hydrogenation section [A] to the sum of mole fractions of cyclohexanol, cyclohexanone and phenol in the vapor flow leaving the hydrogenation section [A] is equal to that in the Comparative Example. The heat transfer units [C] and [F] and cooling unit [D] each consist of a series of shell-and-tube type indirect heat exchangers. The hydrogenation product stream leaving the hydrogenation section [A] has a temperature and a pressure that are almost equal to that in the Comparative Example. In cooling unit [D] cooling water is used as coolant and flows on the outside of the tubes of the heat exchangers of the cooling unit [D]. The hydrogenation product stream leaving the cooling unit [D] is at a temperature of 43° C. and is fed as a two-phase system to the gas-liquid separation section [E].

In the gas-liquid separation section [E] the gas phase and the liquid phase are separated in a gas-liquid separation vessel without additional reduction of pressure. The separated gas phase is re-used in the hydrogenation section [A]. Prior to re-use of this flow a fraction is purged in order to prevent the build-up of inert compounds, for example methane or nitrogen. The remaining gas flow is re-pressurized before being fed, via heat transfer unit [C], where it was heated by the hydrogenation product stream leaving the hydrogenation section [A] to a temperature almost equal to that in the Comparative Example, to the hydrogenation section [A]. The liquid phase obtained in the gas-liquid separation vessel is heated in heat transfer unit [F] by the hydrogenation product stream leaving heat transfer unit [C] to about the same temperature as that in the Comparative Example before being charged to first distillation section [G1].

The gaseous flow that is discharged from cyclohexanol dehydrogenation section [G5] via line [123] was cooled in a series of indirect heat exchangers (not shown in FIG. 5) to about 43° C. The resulting cooled flow consists of a liquid phase comprising mainly cyclohexanone, cyclohexanol, by-products and of a hydrogen-containing gas phase. The cooled flow is then passed into a gas-liquid separation section (not shown in FIG. 5) in which it is split into a hydrogen-containing second gas phase and a second liquid phase comprising mainly cyclohexanone, cyclohexanol and by-products. The obtained second liquid phase is, after being heated to about 100° C. (not shown in FIG. 5), charged to a first distillation section [G1] via line [123b]. The hydrogen-containing second gas phase is discharged via line [123a].

Results are shown in Table 1.

Example 3

A cyclohexanone plant analogous to that of Example 2 is used, except that there is no separate preheating of the second liquid phase; which is instead passed, not directly to the first distillation section [G1], but to the in process heat transfer unit [F]. The set-up is therefore substantially as depicted in FIGS. 4 and 6. It is operated at an hourly mass flow of a mixture of cyclohexanone and cyclohexanol (comprising about 99.9 wt % cyclohexanone) leaving the second distillation section [G2], via line [526], of about 25 metric tons.

The ratio of the sum of mole fractions of cyclohexanol and cyclohexanone in the vapor flow leaving the hydrogenation section [A] to the sum of mole fractions of cyclohexanol, cyclohexanone and phenol in the vapor flow leaving the hydrogenation section [A] is equal to that in the Comparative Example. The heat transfer units [C] and [F] and cooling unit [D] all consist of a series of shell-and-tube type indirect heat exchangers. The hydrogenation product stream leaving the hydrogenation section [A] has a temperature and a pressure that are almost equal to that in the Comparative Example. In cooling unit [D] cooling water is used as coolant and flows on the outside of the tubes of the heat exchangers of the cooling unit [D]. The hydrogenation product stream leaving the cooling unit [D] is at a temperature of 43° C. and is fed as a two-phase system to the gas-liquid separation section [E].

In the gas-liquid separation section [E] the gas phase and the liquid phase are separated in a gas-liquid separation vessel without additional reduction of pressure. The separated gas phase is re-used in the hydrogenation section [A]. Prior to re-use of this flow a fraction is purged in order to prevent the build-up of inert compounds, for example methane or nitrogen. The remaining gas flow is re-pressurized before being fed, via heat transfer unit [C], where it is heated by the hydrogenation product stream leaving the hydrogenation section [A] to a temperature almost equal to that in the Comparative Example, to the hydrogenation section [A]. The liquid phase obtained in the gas-liquid separation vessel is heated in heat transfer unit [F] by the hydrogenation product stream leaving heat transfer unit [C] to about the same temperature as that in the Comparative Example before being charged to first distillation section [G1].

The gaseous flow that is discharged from cyclohexanol dehydrogenation section [G5] via line [523] was cooled in a series of indirect heat exchangers (not shown in FIG. 5) to about 43° C. The resulting cooled flow consists of a liquid phase comprising mainly cyclohexanone, cyclohexanol, by-products and of a hydrogen-containing gas phase. The cooled flow was then passed into a gas-liquid separation section (not shown in FIG. 5) in which it is split into a hydrogen-containing second gas phase and a second liquid phase comprising mainly cyclohexanone, cyclohexanol and by-products. The obtained second liquid phase is fed to heat transfer unit [F] via line [523b]. In heat transfer unit [F] it is mixed with the first liquid phase and the combined liquid phases are heated by the hydrogenation product stream leaving heat transfer unit [C]. The hydrogen-containing second gas phase is discharged via line [523a].

Results are shown in Table 1.

TABLE 1

| Example no. | Heat transferred from steam in heating unit [B] in GJ/hr | In-process heat transferred in heat transfer unit [C] in GJ/hr | Heat transferred from steam in heat transfer unit [F] in GJ/hr | In-process heat transferred in heat transfer unit [F] in GJ/hr | Heat transferred to cooling water in cooling unit [D] in GJ/hr | Total steam savings in GJ/hr |
|---|---|---|---|---|---|---|
| Comp. Ex. | 2.0 | 0 | 3.2 | 0 | 25.9 | 0 |
| Example 1 | 0 | 2.0 | 3.2 | 0 | 23.9 | 2.0 |

TABLE 1-continued

| Example no. | Heat transferred from steam in heating unit [B] in GJ/hr | In-process heat transferred in heat transfer unit [C] in GJ/hr | Heat transferred from steam in heat transfer unit [F] in GJ/hr | In-process heat transferred in heat transfer unit [F] in GJ/hr | Heat transferred to cooling water in cooling unit [D] in GJ/hr | Total steam savings in GJ/hr |
|---|---|---|---|---|---|---|
| Example 2 | 0 | 2.0 | 0 | 3.2 | 20.7 | 5.2 |
| Example 3 | 0 | 2.0 | 0 | 3.6 | 20.3 | 5.6 |

Example 1 clearly shows that by introducing an in-process heat transfer unit [C] in place of heating unit [B] the total steam consumption can be reduced by about 2.0 GJ/hr, compared to the conventional method as described in the Comparative Experiment. In addition it is shown that by introducing the in-process heat transfer unit [C] the heat transferred to cooling water in cooling unit [D] is reduced by about 8%, compared to the conventional method as described in the Comparative Experiment.

Example 2 clearly shows that by introducing in-process heat transfer units [C] and [F] the total steam consumption can be reduced by about 5.2 GJ/hr, compared to the conventional method as described in the Comparative Experiment. In addition it is shown that by introducing in-process heat transfer units [C] and [F] the heat transferred to cooling water in cooling unit [D] is reduced by about 20%, compared to the conventional method as described in the Comparative Experiment.

Example 3 clearly shows that by utilizing in-process heat transfer unit [F] to heat the second liquid phase the steam consumption can be further reduced by about 0.4 GJ/hr, compared to the process of Example 2. In other words, the total steam consumption can be reduced by about 5.6 GJ/hr, compared to the conventional method as described in the Comparative Experiment. In addition it is shown that by introducing the in-process heat transfer units [C] and [F] in this way the heat transferred to cooling water in cooling unit [D] is reduced by about 22%, compared to the conventional method as described in the Comparative Experiment.

The invention claimed is:

1. A process for continuously preparing a mixture of cyclohexanone and cyclohexanol comprising:
   a) conducting vapor phase hydrogenation of phenol with gaseous hydrogen, in the presence of platinum or palladium, in a vapor phase hydrogenation reactor, to produce a vapor phase hydrogenation product stream comprising cyclohexanone, cyclohexanol, phenol and hydrogen;
   b) cooling the vapor phase hydrogenation product stream to a temperature such that a fraction of phenol by mass in a first gas phase is lower than a fraction of phenol by mass in a first liquid phase;
   c) separating the first gas phase from the first liquid phase;
   d) returning at least part of the first gas phase to the vapor phase hydrogenation reactor;
   e) heating the first liquid phase;
   f) purifying the first liquid phase by distillation; wherein the process further comprises transferring heat by an in-process heat exchange from the vapor phase hydrogenation product stream in step b) to at least part of the first gas phase in step d) and/or the first liquid phase in step e).

2. A process according to claim 1, wherein the mixture of cyclohexanol and cyclohexanone comprises at least 99.5 wt % cyclohexanone.

3. A process according to claim 1, wherein the mixture of cyclohexanol and cyclohexanone comprises at least 99.85 wt % cyclohexanone.

4. A process according to claim 1, wherein step f) comprises:
   f1) removing a light fraction by distillation;
   f2) recovering as overhead product a mixture of cyclohexanone and cyclohexanol;
   f3) recovering as overhead product a fraction comprising at least 50 wt % cyclohexanol;
   f4) recovering as overhead product a phenol-containing fraction;
   f5) returning at least a part of the phenol-containing fraction to the hydrogenation reactor; and
   f6) removing as bottom product a heavy fraction.

5. A process according to claim 4, further comprising partially converting to cyclohexanone the cyclohexanol in the fraction comprising at least 50 wt % cyclohexanol.

6. A process according to claim 5, further comprising:
   i) cooling the partially converted fraction comprising at least 50 wt % cyclohexanol to form a second liquid phase and a second gas phase;
   ii) separating the second gas phase;
   iii) heating the second liquid phase; and
   iv) purifying the second liquid phase by distillation.

7. A process according to claim 6, which comprises combining the second liquid phase with the first liquid phase to form a combined liquid phase; and transferring heat from the hydrogenation product stream in step b) to the combined liquid phase in step e) by an in-process heat exchange.

8. A process according to claim 1, comprising further converting the mixture of cyclohexanone and cyclohexanol into caprolactam or adipic acid.

9. A process according to claim 1, wherein the hydrogenation product is cooled in step b) to a temperature of from 5 to 80° C.

10. A process according to claim 1, wherein the at least part of the first gas phase is heated to a temperature of from 50 to 200° C.

11. A process according to claim 1, wherein the first liquid phase is heated in step e) to a temperature of from 50 to 200° C.

* * * * *